(12) United States Patent
Li et al.

(10) Patent No.: US 7,875,590 B2
(45) Date of Patent: Jan. 25, 2011

(54) INJECTABLE SOLID HYALURONIC ACID CARRIERS FOR DELIVERY OF OSTEOGENIC PROTEINS

(75) Inventors: Rebecca H. Li, Bedford, MA (US); Hyun D. Kim, Bedford, MA (US)

(73) Assignees: Wyeth, Madison, NJ (US); Fidia Advanced Biopolymers, S.R.L., Padua (IT)

( * ) Notice: Subject to any disclaimer, the term of this patent is extended or adjusted under 35 U.S.C. 154(b) by 0 days.

(21) Appl. No.: 12/414,715

(22) Filed: Mar. 31, 2009

(65) Prior Publication Data

US 2009/0181058 A1    Jul. 16, 2009

Related U.S. Application Data (62) Division of application No. 10/525,441, filed as application No. PCT/US03/14609 on May 12, 2003, now abandoned.

(60) Provisional application No. 60/381,590, filed on May 17, 2002.

(51) Int. Cl.
A61K 38/00 (2006.01)
A61F 2/28 (2006.01)

(52) U.S. Cl. .................................. 514/16.7; 424/426

(58) Field of Classification Search ................. None
See application file for complete search history.

(56) References Cited

U.S. PATENT DOCUMENTS

| | | | |
|---|---|---|---|
| 3,955,719 | A | 5/1976 | Pheulpin |
| 4,784,055 | A | 11/1988 | Langen et al. |
| 4,851,521 | A | 7/1989 | della Valle et al. |
| 4,957,744 | A | 9/1990 | della Valle et al. |
| 5,118,667 | A | 6/1992 | Adams et al. |
| 5,124,316 | A | 6/1992 | Antoniades et al. |
| 5,308,889 | A | 5/1994 | Rhee et al. |
| 5,336,767 | A | 8/1994 | della Valle et al. |
| 5,352,715 | A | 10/1994 | Wallace et al. |
| 5,356,629 | A | 10/1994 | Sander et al. |
| 5,464,440 | A | 11/1995 | Johansson |
| 5,510,121 | A | 4/1996 | Rhee et al. |
| 5,645,592 | A | 7/1997 | Nicolais et al. |
| 5,716,413 | A | 2/1998 | Walter et al. |
| 5,752,974 | A | 5/1998 | Rhee et al. |
| 5,939,323 | A | 8/1999 | Valentini et al. |
| 5,942,499 | A | 8/1999 | Radomsky |
| 6,015,801 | A | 1/2000 | Daifotis et al. |
| 6,187,742 | B1 | 2/2001 | Wozney et al. |
| 6,221,958 | B1 | 4/2001 | Shalaby et al. |
| 6,281,195 | B1 | 8/2001 | Rueger et al. |
| 6,699,471 | B2 | 3/2004 | Radice et al. |
| 7,189,392 | B1 | 3/2007 | Kim et al. |

FOREIGN PATENT DOCUMENTS

| | | |
|---|---|---|
| CZ | 283073 B6 | 12/1997 |
| JP | 2000-202024 | 7/2000 |
| WO | WO 91/17777 | 11/1991 |
| WO | WO 93/20858 | 10/1993 |
| WO | WO 97/32591 | 9/1997 |
| WO | WO 97/45532 | 12/1997 |
| WO | WO 97/49412 | 12/1997 |
| WO | WO 99/24070 | 5/1999 |
| WO | WO 00/16818 | 3/2000 |
| WO | WO 00/37124 | 6/2000 |
| WO | WO 01/28602 | 4/2001 |

OTHER PUBLICATIONS

K.P. Vercruysse and G.D. Prestwich. Hyaluronate Derivatives in Drug Delivery, Critical Review in Therapeutic Drug Carrier Systems. (1998) 15(5), pp. 513-555.*

N.H. Bell and R.H. Johnson. Bisphosphonates in the Treatment of Osteoporosis. Endochrine. (1997) 6(2), pp. 203-206.*

U.S. Appl. No. 10/525,441, filed Feb. 22, 2005, Li et al., co-pending application.

U.S. Appl. No. 10/937,364, filed Sep. 10, 2004, Li et al., co-pending application.

Aigner et al., "Cartilage Tissue Engineering with Novel Nonwoven Structured Biomaterial Based on Hyaluronic Acid Benzyl Ester", *J Biomed Mater Res* 42:172-181 (1988).

Bonucci et al., "Prevention of Ovariectomy Osteopenia in Rats after Vaginal Administration of Hyaff 11 Microspheres Containing Salmon Calcitonin", *Calcif Tissue Int* 56:274-279 (1995).

Brun et al., "Chondrocyte Aggregation and Reorganization into Three-Dimensional Scaffolds", *J Biomed Mat Res* 46:337-46 (1999).

Campoccia et al., "Semisynthetic Resorbable Materials from Hyaluronan Esterification", *Biomaterials*, 19:2101-27 (1998).

Common Organic Solvents: Table of Properties, www.organicdivision.org/organic_solvents.html (Oct. 20, 2007).

Fleisch, Bisphosphonates in bone disease, From the Laboratory to the patient, 3rd Ed. Parthenon Publishing (1997).

Ghezzo et al., "Hyaluronane Derivative Microspheres as NGF Delivery Devices: Preparation Methods and In Vitro Release Characterization", *Int J Pharmaceutics* 87:21-29 (1992).

Illum et al., "Hyaluronic Acid Ester Microspheres as a Nasal Delivery System for Insulin", *J Controlled Release* 29(1-2):133-141 (1994).

International Preliminary Examination Report for PCT/US2003/014609, dated Apr. 13, 2005.

International Search Report for PCT/US2003/014609, dated Apr. 9, 2004.

Kubler et al., "Bone Morphogenetic Protein-Mediated Interaction of Periosteum and Diaphysis", *Clin Osteoped Rel Res* 258:279-94 (1990).

Solchaga et al., "Hyaluronic Acid-Based Polymers as Cell Carriers or Tissue-Engineered Repair of Bone and Cartilage", *J Orthopaedic Res* 17:205-213 (1999).

Supplementary European Search Report, EP 03 72 6735.8, dated Sep. 5, 2007.

* cited by examiner

*Primary Examiner*—Andrew D Kosar
(74) *Attorney, Agent, or Firm*—Finnegan, Henderson, Farabow, Garrett & Dunner, LLP (57) ABSTRACT

Methods of using an injectable or implantable rod-shaped formulation for delivery of osteogenic proteins to treat osteoporotic and/or osteopenic bone are disclosed. The formulation comprises hyaluronic acid derivatives and osteogenic proteins, and optional excipients and active ingredients such as a bone resorption inhibitor.

27 Claims, 1 Drawing Sheet

Figure 1

INJECTABLE SOLID HYALURONIC ACID CARRIERS FOR DELIVERY OF OSTEOGENIC PROTEINS

CROSS REFERENCE TO RELATED APPLICATIONS

This is a division of application Ser. No. 10/525,441, filed Feb. 22, 2005, which is a National Stage Entry of PCT/US03/14609, filed May 12, 2003, now abandoned, which claims the benefit of U.S. Provisional Application No. 60/381,590, filed May 17, 2002, all of which are incorporated herein by reference.

FIELD OF THE INVENTION

The subject invention relates to the field of osteogenic proteins and pharmaceutical formulations thereof. More particularly, the subject invention involves injectable or implantable solid pharmaceutical formulations comprising hyaluronic acid derivatives and osteogenic proteins.

BACKGROUND OF THE INVENTION

Idiopathic osteoporosis is a disease of unknown etiology characterized by progressive loss of bone mass and increased fragility, resulting in a marked increase in susceptibility to fractures. Osteoporosis is among the most prevalent of all musculoskeletal disorders, afflicting fifty-six percent of women over 45 years of age. Praemer et al., Musculoskeletal Conditions in the United States, American Academy of Orthopaedic Surgeons, Park Ridge, Ill. (1992). Because its incidence increases with age and the percentage of elderly in the population is increasing, osteoporosis will become more common with time. Osteoporosis is difficult to treat locally, and there is presently no known cure. Finally, and most significantly, osteoporosis is associated with a substantial morbidity and mortality. The most serious fracture resulting from osteoporosis is that of the proximal femur in the region of the hip joint. With an annual incidence of over 300,000, hip fractures are currently the most common fracture in the elderly. One out of every six Caucasian women will have a hip fracture during her lifetime (Cummings et al., Arch Intern Med 149:2455-2458 (1989)), and for those who attain the age of 90, this figure becomes one in three.

Of the patients who are independent and living at home at the time of hip fracture, approximately 20 percent remain in a long term care institution for at least one year following the fracture. During the first year following injury, the mortality rate is approximately 15% higher than for age and gender matched controls. Praemer et al., supra. The increased incidence of proximal femur fracture observed in elderly patients is mainly related to a decreased bone density of their proximal femora, as well as an increased propensity to fall. There is an inverse relationship between the age-related bone loss in the proximal femur and the risk of hip fracture. Each decrease of one standard deviation (SD) in femoral neck bone density increases the age-adjusted risk of hip fracture 2.6 times (95% Cl 1.9-3.6), and women with bone density in the lowest quartile have an 8.5-fold greater risk of hip fracture than those in the highest quartile. Cummings et al., The Lancet 341:72-75 (1993). This relation between hip bone mass and hip fracture risk allows the screening and identification of patients at risk for fracture. Patients who are two standard deviations below peak hip bone mass have passed beneath the "fracture threshold."

Current therapies for osteoporosis are systemic. These include fluoride, bisphosphonates, calcitonin, estrogens and progestins, testosterone, vitamin D metabolites, and/or calcium. In the United States, only estrogens and alendronate, a bisphosphonate, are indicated for the prevention of hip fractures in postmenopausal osteoporotic women. Each of these agents requires continuous administration over a time period of years.

In addition to treating osteoporotic bone, a need exists for methods of treating or preventing osteoporosis-related fractures, for example by local administration of osteogenic proteins. Because of this need, despite the variety and availability of carrier materials for delivering osteogenic proteins, a need also exists for safe, effective and generally applicable carriers for local treatment of bone defects. Accordingly, despite substantial endeavors in this field, there remains a need for an effective method of repair and/or treatment of osteoporotic and osteopenic bone, and for minimizing or reducing the incidence or severity of osteoporosis-related fractures.

SUMMARY OF THE INVENTION

The present invention provides injectable or implantable solid, rod-shaped compositions for intraosseous delivery of osteogenic proteins. In one embodiment, the composition comprises the osteogenic protein and hyaluronic acid esters. In another embodiment, the composition may further comprise a bone resorption inhibitor such as a bisphosphonate. In yet another embodiment, the composition may further comprise one or more excipients, such as a pharmaceutically acceptable salt, polysaccharide, peptide, protein, amino acid, synthetic polymer, natural polymers, or surfactant. The solid, rod-shaped injectable or implantable compositions of the invention provide prolonged retention of the osteoinductive agent at the site of administration.

The present invention further provides methods and compositions for increasing bone mass and quality, and for minimizing or reducing the incidence or severity of osteoporosis-related fractures. Accordingly, the present invention provides methods and compositions useful for decreasing the incidence of fractures of osteoporotic or osteopenic bone. In particular, the present invention comprises methods of treating patients with osteoporosis, or with other evidence of osteoporosis or osteopenic condition. Preferred embodiments where the present invention may prove particularly useful include treatment of metaphyseal bone, including proximal femur (hip), proximal humerus (upper arm), distal radius (wrist), and vertebral bodies (spine), particularly the vertebral body.

The method comprises administering to a site of osteopenic or osteoporotic bone, or a site of low bone mass or density, a solid rod-shaped composition comprising an effective amount of at least one active agent that is capable of inducing growth of bone or increasing the formation of bone tissue or reducing bone loss at the site. Bone mass is commonly designated "bone mineral content" or "BMC" and is measured in grams. Bone density is commonly designated "bone mineral density" or "BMD" and is expressed as grams per unit area or grams per unit volume. In a particular embodiment, the mode of administration is by intraosseous injection. In illustrative embodiments, the active agent is one or more proteins selected from the group of proteins known as the transforming growth factors-beta ("TGF-β") superfamily of proteins, preferably selected from the bone morphogenetic proteins ("BMPs"), the growth and differentiation factors ("GDFs"), as well as other proteins, as described more fully herein. The methods and compositions of the present invention are advantageous in that they provide a localized treatment for osteoporosis or osteopenic bone, rather than systemic treatment. The present invention is further advantageous in that it utilizes as active agents osteogenic proteins, which may be produced via recombinant DNA technology, and therefore are of potentially unlimited supply. The methods and compositions of the present invention are further advantageous in that regeneration of the bone tissue increases the bone mass/density, increase the bone strength, and thereby reduce the severity of osteoporosis or incidence of osteoporotic lesions, ultimately lessening the incidence of bone fractures.

In other embodiments, the active agent further comprises, in addition to one or more proteins selected from the TGF-β superfamily of proteins, one or more auxiliary proteins, such as Hedgehog, Noggin, Chordin, Frazzled, Cerberus and Follistatin, soluble BMP receptors, or other protein or agent, as described further herein.

The present invention further provides a methods for increasing bone mass and quality, and for minimizing or reducing the incidence or severity of osteoporosis-related fractures, by administering an injectable rod-shaped composition comprising at least one osteogenic protein and a second composition comprising an effective amount of a bone resorption inhibitor. The second composition comprising the bone resorption inhibitor may be administered prior to, after, or substantially simultaneously with the osteogenic composition.

In addition to healing of osteoporotic bone, compositions of the present invention may be useful for injectable formulations of BMPs for uses such as injection into joints for treatment and repair of osseous defects, cartilage defects, inhibition of cartilage degradation and to promote cartilage repair. The formulations may also be injected into tendons, ligaments and/or their attachment sites to bone. Injectable formulations of BMPs may also find application to other bone sites such as bone cysts, implants into bones, closed or open fractures and distraction osteogenesis.

In a particular embodiment, the compositions of the present invention are prepared by a process comprising the steps of mixing an osteogenic protein and a hyaluronic acid derivative to form an osteogenic mixture. The osteogenic mixture is then formed, for example by extruding the osteogenic mixture into air or a nonsolvent such as ethanol, and drying. The compositions of the invention may further comprise a bone resorption inhibitor and/or an excipient, either or both of which may be included in the mixing step.

The hyaluronic acid derivative may be a natural or synthetic hyaluronic acid, or a modification thereof. Hyaluronic acid is a naturally-occurring polysaccharide containing alternating N-acetyl-D-glucosamine and D-glucuronic acid monosaccharide units linked with beta 1-4 bonds and the disaccharide units linked with beta 1-3 glycoside bonds. It occurs usually as the sodium salt and has a molecular weight range of about 50,000 to $8 \times 10^6$. The bone resorption inhibitor may be a bisphosphonate, such as alendronate, cimadronate, clodronate, EB-1053, etidronate, ibandronate, neridronate, olpadronate, pamidronate, risedronate, tiludronate, YH 529, zoledronate, and pharmaceutically acceptable salts, esters, and mixtures thereof. The excipient may be an agent that stabilizes and/or modulates release of the active ingredient(s), such as a pharmaceutically acceptable salt, polysaccharide, peptide, protein, amino acid, synthetic polymer, natural polymers, and/or surfactant. The osteogenic protein can be in a solid or liquid form, and the hyaluronic acid derivative and excipient(s) can be in a solid form. The molding may be accomplished by extruding the osteogenic mixture into air or a nonsolvent such as ethanol; the drying may accomplished by air-drying or freeze-drying. The sustained-release preparation may further comprise a bone resorption inhibitor such as a bisphosphonate.

The present invention also provides a method for preparing an injectable sustained-release preparation comprising the steps of admixing an osteogenic protein with a hyaluronic acid or hyaluronan-based material to form an admixture, compressing the admixture to form a dense osteogenic admixture, then forming the dense osteogenic admixture into a solid cylindrical rod suitable for injecting or implanting into a body. The forming step may be performed by extruding, pressing, molding, boring and/or cutting to form a cylindrical rod. The injectable sustained-release preparation may further comprise a bone resorption inhibitor, such as a bisphosphonate, and one or more excipients, such as those described above.

The injectable, solid, osteoinductive compositions of the present invention may have a diameter of between about 0.1 to 3.0 mm, and preferably between about 0.5 to 1.5 mm. The length of the solid rod-shaped compositions may be between about 1 mm and about 10 cm, and particularly between about 2 cm and about 5 cm. The compositions of the present invention may have a height to diameter ratio within the range of about 1000:1 to 1:1. This ratio may be about 1000:1, 500:1, 250:1, 100:1, 50:1, 25:1, 10:1, 5:1, 4:1, 3:1, 2:1 or 1:1. The osteoinductive compositions of the present invention are rigid (but not brittle) to withstand loading into a conventional needle or syringe, and injection into an intraosseous site. The osteoinductive compositions have a density of between about 0.5 and 100 percent material, and preferably of between about 50 and 90 percent material. The compositions have a low macroporosity and a low water content, between about 0.1 and about 10.0 percent water, and particularly between about 0.1 and about 5 percent water. The proportion of active ingredient to carrier may be between about 0.01-0.90 gram of active ingredient to about 1 gram of carrier, and particularly between 0.1-0.3 gram of active ingredient to about 1 gram of carrier. The hyaluronic acid derivative may be a partial or full ester comprising between about 50 and about 100 percent hyaluronic acid esterification.

DESCRIPTION OF THE EMBODIMENTS

According to the present invention, methods and compositions are provided for treatment of patients who exhibit signs of osteoporosis, or osteopenic conditions, including osteoporotic bone lesions. The identification of such patients may be accomplished by procedures that are well known in the art. These procedures include measurement of bone mass/density using dual-energy X-ray absorptiometry (DEXA), Kilgus et al., J. Bone & Joint Surgery, 75-B:279-287 (1992); Markel et al., Acta Orthop. Scand. 61:487-498 (1990); and quantitative computed tomography (QCT), Laval-Jeantet et al., J. Comput. Assist. Tomogr., 17:915-921 (1993); Markel, Calcif. Tissue Int. 49:427-432 (1991); single-photon absorptiometry, Markel et al., Calcif. Tissue Int. 48:392-399 (1991); ultrasound transmission velocity (UTV); Heaney et al., JAMA 261:2986-2990 (1989); Langton et al., Clin. Phys. Physiol. Meas. 11:243-249 (1990); and radiographic assessment, Gluer et al., J. Bone Min. Res. 9:671-677 (1994). Other methods of identification of patients at risk of bone fracture include assessment of age-related factors, such as cognisance, as well as prior occurrence of osteoporosis-related fractures. Porter et al., BMJ 301:638-641 (1990); Hui et al., J. Clin. Invest. 81:1804-1809 (1988). The above publications are hereby incorporated by reference herein.

The methods comprise injecting into the osteoporotic or osteopenic site a solid rod-shaped composition comprising one or more purified osteogenic proteins, which is effective to induce the formation and/or maintenance of bone, and a hyaluronic acid as a carrier. Unlike existing injectable formulations, the osteogenic composition of the present invention is administered in a solid form, thereby avoiding the deficiencies inherent in liquid or viscous formulations. For example, using liquid or gel formulations, the osteoinductive agent may be prematurely diluted by the body fluids before the bone promoting effect can be achieved. The present invention obviates the dilution effect by employing a solid carrier that degrades slowly in vivo, thereby providing delayed, sustained release of the active ingredient(s). Furthermore, unlike liquid or viscous formulations that may migrate from the site of administration, the solid compositions of the present invention become lodged and persist at the site of desired bone growth to effect the bone growth promoting activity. Typically, the composition must persist at the site for a period from about seven days to about six months. If the composition is dispersed prematurely, the desired bone growth-promotion effect either will not occur or the formed bone will not have the desired strength. Finally, although the osteogenic composition of the present invention is administered as a solid, it is formed as a cylindrical rod, thereby being suitable for either injection or implantation into the body. In addition, the well-known surgical complication of inducing an embolism during an intraosseous injection procedure is considerably mitigated through the use of solid rods (vs. liquid or gel forms). The potential displacement of intraosseous bone fragments, fat or an embolism caused by a pressurized injection of a large volume of liquid/gel carrier is reduced since the volume injected of highly concentrated solid rod carrier is much less than that required if a similar dose was dispensed in a liquid or gel form. The composition may be applied to the site of desired bone growth in any convenient manner, including by introduction through a conventional hypodermic needle or syringe.

The compositions of the present invention are prepared by mixing the osteogenic protein, hyaluronic acid carrier and optional excipients to form, depending upon the hyaluronic acid starting material, either a viscous liquid/gel or paste. The ensuing mass is then shaped into cylindrical rods and dried. The shaping may be accomplished using any one of a number of known techniques, for example by molding, pressing, boring and/or cutting. In a preferred embodiment, the osteogenic mixture is packed into and extruded through the hub end of a hypodermic syringe. The material is extruded as continuous cylindrically shaped rods, dried at room temperature and sectioned into small, injectable rods.

If the hyaluronic acid starting material is a hydrophobic solid, such as HYAFF-11®, the hyaluronic acid is first solubilized in an organic solvent to form a solution. The organic solvent may be any pharmaceutically acceptable solvent, such as N-methylpyrrolidone (NMP) or dimethyl sulfoxide (DMSO), preferably NMP. The solution may comprise between about 1 and about 50% (w/v) hyaluronic acid, preferably between about 5 and 20% (w/v), and most preferably about 10% (w/v) hyaluronic acid. The dry powdered osteogenic protein is dispersed in the hyaluronic acid solution at a concentration of between about 1 and about 50% (w/w), preferably about 20% (w/w), and optional excipients (e.g., amino acids, sugars, salts, surfactants, polymers, etc.) are added at a concentration of between about 1 and about 50% (w/w), preferably between about 20 and about 40% (w/w). The compositions of the invention may further comprise a bone resorption inhibitor, which may be included in the mixing step in dry powder or soluble form, individually or in combination with the osteogenic protein component.

If the hyaluronic acid starting material is in a hydrophilic form, such as HYAFF-11P65®, the hyaluronic acid may be blended with an aqueous buffer comprising optional excipients until the mass assumes a paste-like consistency. The paste-like substance may comprise between about 1 and about 40% (w/v), preferably between about 5 and about 30% (w/v), and more preferably between about 15 and about 20% (w/v) hyaluronic acid. In an exemplified embodiment, the paste-like substance comprises 18.75% (w/v) hyaluronic acid. The dry powdered osteogenic protein is then mixed into the hyaluronic acid paste prior to shaping. Alternatively, rather than blending with an aqueous buffer comprising optional excipients, the hyaluronic acid starting material may be blended with an aqueous buffer comprising soluble osteogenic protein with optional excipients until the mass assumes a paste-like consistency or a viscous liquid or gel appearance. The compositions may further comprise a bone resorption inhibitor, which may be included in the mixing step in dry powder or soluble form, individually or in combination with the osteogenic protein component.

Once the components have been combined and blended into a paste or viscous liquid or gel, the osteogenic material is packed into a cylindrical mold, air or gas-permeable tubing (e.g., silastic or TEFLON®/FEP), or extrusion type apparatus, such as a syringe. If a syringe is used for the forming step, the plunger of the syringe is inserted and a sufficient amount of pressure is applied to extrude a continuous length of paste onto a dry surface, in the case of water soluble hyaluronic acid. In the case of water insoluble hyaluronic acid, a continuous length of gel is extruded into a nonsolvent bath enabling precipitation of the material. Sections are then cut using a cutting tool such as a razor, scalpel, knife or the like, to form injectable, rod-shaped compositions. After sectioning, the rod-shaped compositions are dried, for example by air drying or freeze drying.

The present invention also provides a method for preparing an injectable sustained-release preparation comprising the steps of admixing an osteogenic protein, a hyaluronic acid or hyaluronan-based material, and optional excipients to form a dense osteogenic admixture, then forming the dense osteogenic admixture into a solid cylindrical rod suitable for injecting or implanting into a body.

The active agent can be selected from the family of proteins known as the transforming growth factors-beta (TGF-β) superfamily of proteins, which includes the activins, inhibins and bone morphogenetic proteins (BMPs). Particularly, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO 91/18098; and BMP-9, disclosed in PCT publication WO 93/00432, BMP-10, disclosed in PCT application WO 94/26893; BMP-11, disclosed in PCT application WO 94/26892, or BMP-12 or BMP-13, disclosed in PCT application WO 95/16035; BMP-15, disclosed in U.S. Pat. No. 5,635,372; or BMP-16, disclosed in U.S. Pat. No. 6,331,612. Other TGF-β proteins that may be useful as the active agent in the present invention include Vgr-2, Jones et al., Mol. Endocrinol. 6:1961-1968 (1992), and any of the growth and differentiation factors (GDFs), including those described in PCT applications WO 94/15965; WO 94/15949; WO 95/01801; WO 95/01802; WO 94/21681; WO 94/15966; WO 95/10539; WO 96/01845; WO 96/02559 and others. Also useful in the present invention may be BIP, disclosed in WO 94/01557; HP00269, disclosed in JP Publication number: 7-250688; and MP52, disclosed in PCT application WO 93/16099. The disclosures of all of the above applications are hereby incorporated by reference. A subset of BMPs that are presently preferred for use in the present invention include BMP-2, BMP-4, BMP-5, BMP-6, BMP-7, BMP-10, BMP-12 and BMP-13. In an illustrative embodiment, the active agent is BMP-2, the sequence of which is disclosed in U.S. Pat. No. 5,013,649, the disclosure of which is hereby incorporated by reference. Other BMPs and TGF-β proteins known in the art can also be used.

The active agent may be recombinantly produced, or purified from a protein composition. The active agent, if a TGF-β such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is hereby incorporated herein by reference.

The active agent may further comprise additional agents such as the Hedgehog, Frazzled, Chordin, Noggin, Cerberus and Follistatin proteins. These families of proteins are generally described in Sasai et al., Cell, 79:779-790 (1994) (Chordin); PCT Patent Publication WO 94/05800 (Noggin); and Fukui et al., Dev. Biol. 159:131-139 (1993) (Follistatin). Hedgehog proteins are described in WO 96/16668; WO 96/17924; and WO 95/18856. The Frazzled family of proteins is a relatively recently discovered family of proteins with high homology to the extracellular binding domain of the receptor protein family known as Frizzled. The Frizzled family of genes and proteins is described in Wang et al., J. Biol. Chem. 271:4468-4476 (1996). The active agent may also include other soluble receptors, such as the truncated soluble receptors disclosed in PCT patent publication WO 95/07982. From the teaching of WO 95/07982, one skilled in the art will recognize that truncated soluble receptors can be prepared for numerous other receptor proteins. Such would also be encompassed within the present invention. The above publications are hereby incorporated by reference herein.

The amount of active agent useful herein is that amount effective to stimulate increased osteogenic activity of present or infiltrating progenitor or other cells, and will depend upon the size and nature of the defect being treated. Generally, the amount of protein to be delivered is in a range of from about 0.1 to about 500 mg, particularly about 10 to about 300 mg, and more particularly about 150 to about 250 mg per cubic centimeter of material required.

Materials which may be useful as the carrier in practicing the present invention include pharmaceutically acceptable materials having a rigidity such that, when mixed and dried with a bone morphogenetic protein, form a composition that possesses appropriate handling characteristics for injectable or implantable application to the site of osteoporotic or osteopenic bone. Incorporating the bone morphogenetic protein in a solid carrier allows the protein to remain in the diseased or lesioned site for a time sufficient to allow the protein to increase the otherwise natural rate of regenerative osteogenic activity of the infiltrating mammalian progenitor or other cells, and to form a space in which new tissue can grow and allow for ingrowth of cells. The carrier may also allow the bone morphogenetic protein to be released from the disease or lesion site over a time interval appropriate for optimally increasing the rate of regenerative osteogenic activity of the progenitor cells. The carrier may also supply a framework on which to induce new formation in severely osteoporotic bone.

In illustrative embodiments, the family of carriers comprises hyaluronic acid esters or hyaluronan-based materials. As used herein, the terms "hyaluronic acid," "hyaluronan-based material," and "hyaluronic acid derivatives" are used interchangeably to mean hyaluronic acid (as defined below) and its salts such as the sodium, potassium magnesium calcium and the like, salts. After molding and drying, the hyaluronic acid carriers are in a form suitable for injection or implantation, such as a cylindrical rod, described in detail below. Such rods are rigid enough to withstand loading into a conventional hypodermic needle or syringe, as well as injection into an intraosseous space. Although rigid, the hyaluronic acid-based carrier materials have high tensile strength and low fragility. The solid rod compositions of the invention preferably have a relatively high density of material (30-100%), low macroporosity, and low water content.

Hyaluronic acid occurs naturally in a variety of tissues, including synovial fluid, vitreous humor, human umbilical cord and cocks' combs. It is the main component of the intracellular matrix of connective tissues such as skin, tendons, muscles and cartilage. In addition to providing mechanical support for the cells of these tissues, hyaluronic acid also facilitates other important biological functions, including hydration, lubrication, cellular migration and differentiation (see, e.g., Balazs et al., Cosmetics & Toiletries 5(84):8-17). Hyaluronic acid may be extracted from natural tissues, such as cocks' combs, or produced by recombinant methods. The molecular weight of hyaluronic acid obtained by extraction generally ranges from between 8 and 13 million. The polysaccharide is labile and readily degraded by a variety of physical (mechanical, radiation) and chemical agents. As a result, ordinary purification procedures generally produce hydrolyzed fractions of low molecular weight hyaluronic acids (see Balazs et al., supra).

As used herein, the term "hyaluronic acid" refers to an acidic polysaccharide comprising D-glucuronic acid and N-acetyl-D-glucosamine residues, regardless of molecular weight, including mixtures of various molecular weight fractions and derivatives thereof. Derivatives of hyaluronic acid include, for example, hyaluronic acid that has been chemically modified through esterification, cross-linking, sulphation, etc. The hyaluronic acid may be an ester, such as a methyl ester of a hyaluronic acid as described, for example, in Jeanloz et al., J. Biol. Chem. 186:495-511 (1950); Jager et al., J. Bacteriology 1065-1067; Biochem. J. 167:711-716 (1977); Jeanloz et al., J. Biol. Chem. 194:141-150 (1952); or Jeanloz et al., Helvetica Chimica Acta 35:262-271 (1952).

In an illustrative embodiment, the hyaluronic acid is an ester of hyaluronic acid with aliphatic, aromatic, aroaliphatic, cycloaliphatic or etherocyclic alcohols, in which all or a portion of the carboxylic groups of the acid are esterified, such as the hyaluronic acid derivatives described in U.S. Pat. No. 5,336,767, which is hereby incorporated by reference in its entirety herein. The hyaluronic acid starting materials may be as described in co-pending U.S. application Ser. No. 09/687,283, filed Oct. 13, 2000, which is hereby incorporated by reference in its entirety herein. Preferably, the hyaluronan-based starting materials are solids such as non-woven pads, felts, sheets, powders, sponges, and microspheres sold under the tradename HYAFF® by Fidia Advanced Biopolymers, Abano Terme, Italy. HYAFF® materials are described, for example, in U.S. Pat. Nos. 4,851,521; 4,965,353; and 5,202,431; and EP 0 216 453, all of which are hereby incorporated by reference in their entireties herein. The HYAFF® materials are esters of hyaluronic acid having one or a combination of ester moieties (e.g., benzyl, ethyl, propyl, pentyl, or larger molecules such as hydrocortisone or methyl prednisone), as well as various degrees of esterification (i.e., partial esters or complete esters). Partial esters of HYAFF® materials are designated by percent esterification ranging from 50-99% (e.g., HYAFF-11P65® and HYAFF-11P80®), while complete esters are 100% esters of hyaluronic acid (e.g., HYAFF-11®). In addition to providing the desired handling characteristics of the compositions of the present invention, HYAFF® materials also provide a means for manipulating the bioavailability and absorption kinetics of the active ingredient(s) [see, e.g., U.S. Pat. Nos. 6,339,074; 6,232,303; and 6,066,340, all of which are incorporated by reference in their entireties herein].

In another illustrative embodiment, the hyaluronan-based starting materials are non-woven fabrics comprising mixtures of fibers of hyaluronic acid esters and natural polymers, semi-synthetic derivatives of natural polymers, and/or synthetic polymers. The mixture may comprise from about 1 to about 100% hyaluronic acid. Natural polymers useful in the present invention include, without limitation, collagen, or coprecipitates of collagen and glycosaminoglycans; cellulose; polysaccharides such as chitin, chitosan, pectin or pectic acid, agar, agarose, xanthan gum, gellan, alginic acid or alginates, polymannan or polyglycans, starches, and natural gums. Semisynthetic derivatives of natural polymers useful in the present invention include, for example, natural polymers such as collagen cross-linked with agents such as aldehydes or aldehyde precursors, dicarboxylic acids or halides thereof, diamines, derivatives of cellulose, alginic acid, starch, hyaluronic acid, chitin or chitosan, gellan, xanthan, pectin, or pectic acid, polyglycans, polymannan, agar, agarose, natural gums, and glycosaminoglycans. Synthetic polymers include, for example, polylactic acid, polyglycolic acid, polydioxanes, polyphosphazenes, polysulfone resins, polyurethane resins, and copolymers and derivatives thereof. Exemplary non-woven fabric materials useful in the present invention, including methods of making these materials, are described in U.S. Pat. No. 5,520,916, issued May 28, 1996, which is hereby incorporated by reference in its entirety herein.

Although much is known about the osteogenic potential of TGF-β proteins, recent reports show that local administration of certain osteoinductive agents, such as BMP-2, stimulates transient osteoclastic activity at the site of administration. This reaction, which proceeds new bone formation induced by the BMP, has been termed "transient resorption phenomenon."

Agents known to inhibit bone resorption may play an important role in delaying or reducing the initial bone resorption associated with local BMP administration, without inhibiting the subsequent bone formation. Clinically, bisphosphonate therapy has been shown to dramatically reduce indices of bone turnover, increase bone mineral density, and, in osteopenic women, reduce hip and spine fracture risk (see, e.g., Fleisch, H., Bisphosphonates In Bone Disease, From The Laboratory To The Patient, 3rd Ed., Parthenon Publishing (1997), which is incorporated by reference in its entirety herein). Thus, in one embodiment, a bone resorption inhibitor such as a bisphosphonate is co-administered with the osteoinductive agent to prevent or minimize the initial bone resorption associated with intraosseous delivery of BMP. The co-administration of bisphosphonate blocks this undesirable resorption phase, while still allowing the bone augmentation effect to occur.

Despite their therapeutic benefit, bisphosphonates are poorly absorbed in the gastrointestinal tract when taken orally. To overcome this poor bioavailability issue, intravenous administration has been used; however, this modality is seen as costly and inconvenient due to the duration and frequency of dosing. The present invention overcomes this deficiency by incorporating the bisphosphonate within a carrier, and delivering it locally directly to the site of desired action.

In one embodiment of the invention, the bone resorption inhibitor is incorporated into the injectable osteoinductive composition as a second active ingredient. The bone resorption inhibitor may be mixed with the osteogenic protein, hyaluronic acid carrier, and/or optional excipient(s) prior to the molding and drying steps. The final mixture is then molded, for example by extrusion into a nonsolvent or air.

In another embodiment of the invention, the bone resorption inhibitor is administered sequentially or concurrently with the osteogenic composition. In accordance with this embodiment, the osteogenic composition may be administered locally to a specific area in need of bone growth or repair, with either the concurrent or sequential administration of the bone resorption inhibitor in a separate delivery vehicle. Thus, the bone resorption inhibitor may be injected or implanted directly at the site to be treated, for example, by injection or surgical implantation in a sustained-release carrier. The carrier may be any pharmaceutically acceptable carrier, a wide variety of which are well known and readily available in the art (see, e.g., Martin, E. W., Remington's Pharmaceutical Sciences (Mack Pub. Co., current edition), which is hereby incorporated by reference in its entirety herein). Preferably the carrier is a sustained-release carrier, most preferably the hyaluronic acid esters or hyaluronan-based materials described above. Presently preferred carriers are formed into solid rods, as described elsewhere herein.

As used herein, the term "inhibition of bone resorption" refers to prevention of bone loss, especially the inhibition of removal of existing bone through direct or indirect alteration of osteoclast formation or activity. Thus, the term "bone resorption inhibitor" as used herein refers to agents that prevent or inhibit bone loss by the direct or indirect alteration of osteoclast formation or activity.

As used herein, the term "bisphosphonate" refers to the related bisphosphonic acids and salts, and various crystalline and amorphous forms of bisphosphonate. In a particular embodiment, the bisphosphonate is selected from the group consisting of alendronate, cimadronate, clodronate, EB-1053, etidronates, ibandronate, neridronate, olpadronate, pamidronate, risedronate, tiludronate, YH 529, zolendronate, and pharmaceutically acceptable salts, esters, acids, and mixtures thereof.

The amount of bone resorption inhibitor useful herein is that amount effective to prevent or inhibit the initial bone loss, typically associated with the local administration of BMP, by the direct or indirect alteration of osteoclast formation or activity. The precise dosage necessary will depend upon the size and nature of the defect being treated, as well as the amount of osteogenic agent being delivered. Generally, the amount of phosphonate to be delivered is in a range of from about 1 to about 3000 mg, particularly about 10 to about 1000 mg, and illustratively about 100 to about 500 mg per cubic centimeter of material. The application site is preferably local (intraosseous), but can be other parenteral sites such as intramuscular or subcutaneous for systemic delivery.

Additional additives or excipients that may be useful in the compositions of the present invention include, without limitation, pharmaceutically acceptable salts, polysaccharides, peptides, proteins, amino acids, synthetic polymers, natural polymers, and/or surfactants. Such excipients are well known in the formulation art to stabilize and/or modulate release of the active ingredient(s). Useful polymers include, for example, those described in U.S. Pat. No. 5,171,579, the entire disclosure of which is incorporated herein by reference. Synthetic polymers or surfactants include, without limitation, the pluronics, such as Poloxamer 407 gel, which are a class of water soluble ABA type block surfactant copolymers which exhibit the unique property of reverse thermal gelation. Other useful synthetic polymers include polylactides and polyethylene glycols including poly(lactide)/poly(ethylene glycol), polyvinylpyrrolidone (PVP), poly(ethylene glycol), polyoxyethylene oxide, carboxyvinyl polymer and poly(vinyl alcohol). Natural polymers include, without limitation, sodium alginate, chitosan, collagen, gelatin, hyaluronan, and cellulosic materials, such as hydroxycelluloses. Other useful excipients include peptides, proteins, and amino acids.

In one embodiment of the present invention, the excipient is present in powder form, which is then mixed with the active agent(s) into solubilized HYAFF-11® in organic solvent, and extruded into ethanol (nonsolvent) to form rods, which are then rinsed and dried. The final composition may contain one or a combination of excipients, preferably a salt, sugar (e.g., sucrose) and/or amino acid (e.g., glycine and/or glutamic acid). Preferred compositions of the present invention comprise about 1 to about 60% (w/w) amino acid, about 1 to about 60% (w/w) of a sugar, and about 1 to about 60% (w/w) synthetic polymer. In a preferred embodiment of the invention, the formulation comprises about 20-50% (w/w) amino acid, and/or about 5-50% (w/w) sugar, and/or about 20-50% (w/w) synthetic polymer.

The injectable compositions of the present invention may be administered in any clinically acceptable manner of injection. A number of commercially available syringes may be suitable for use in the present invention, and for administration of the compositions of the present invention. For example, suitable syringes are available the CALASEPT® syringe [JS Dental Manufacturing, Ridgefield Conn.] comprises sterile calcium hydroxide paste in isotonic saline solution, in a non-aspirating or modified aspirating cartridge syringe; HENKE-JECT® aspirating syringe and HYPO® dental syringes/needles [Smith & Nephew MPL, Franklin Park, Ill.]; intraosseous needles from MPL, Inc., Chicago Ill.; and LUER-LOk® Syringes [Becton Dickinson, Franklin Lakes, N.J.], may all be appropriate syringes for use in the present invention. Any syringe capable of holding and delivering an injectable rod and/or enabling extrusion with an obdurator is appropriate for use.

In one embodiment of the invention, the solid rod-shaped compositions are delivered intraosseously using an appropriate size and type hypodermic needle percutaneously or surgically preplaced into the selected anatomic location. Percutaneous placement of the hypodermic needle may be accomplished using manual palpation of known anatomic landmarks, with or without the use of fluoroscopy for visualize placement. Fluoroscopy may also be used in conjunction with surgical implantation prior to and/or concurrent with placement of the hypodermic needle.

In an illustrative embodiment, a guide wire (commonly referred to as a "k-wire") is first inserted percutaneously into the desired anatomic location to serve as a guide for the hypodermic needle. The hypodermic needle is inserted over the guide wire, which is subsequently removed leaving only the hypodermic needle in place. The solid rod-shaped composition is then inserted into the hub end of the hypodermic needle. Following loading of the composition, a second guide wire is inserted into the needle, which is used to advance the solid composition to the tip of the needle. The needle is then removed leaving the guide wire to anchor the composition within the bone at the desired location. Finally, the guide wire is removed leaving the solid composition in place. In another embodiment, the solid rod-shaped composition of the invention is preplaced within the needle barrel. After placement into the desired anatomic site, the plunger of the syringe is advanced into the needle barrel as the device is withdrawn, leaving the solid rod-shaped composition at the desired location.

In one embodiment of the present invention, bone morphogenetic proteins are used as an osteoinductive agent to treat osteoporosis. Patients who might benefit from such treatment may be identified using any one or more of a variety of standard procedures, including measurement of bone mass/density using dual-energy X-ray absorptiometry (DEXA), quantitative computed tomography (QCT), single-photon absorptiometry, ultrasound transmission velocity (UTV), and/or radiographic assessment. Such procedures provide the clinician with information on the location and severity of osteoporotic or osteopenic bone lesions. In addition to locating the lesion(s) to be treated, the clinician can use this information to select the appropriate mode of administration and dose of osteoinductive agent for the patient.

In another embodiment of the present invention, bone morphogenetic proteins are used as an osteoinductive agent in the process known as distraction osteogenesis. This process is an alternative to segmental bone regeneration in response to implanted osteoinductive agents. In traditional segmental bone repair, the osteoinductive agent and carrier are placed in the defect created between the parent bone ends. For bone formation to occur, the osteoinductive agent has to have sufficient residence time in the defect to stimulate differentiation of sufficient numbers of bone forming cells to support new bone formation. The process of distraction osteogenesis creates a regenerate construct between the distracted parent bone ends that is highly vascular and contains a large population of mesenchymal stem cells destined to become bone forming cells. As a result, the regenerate construct represents a much more ideal environment for cell differentiation growth factors such rhBMP-2 to stimulate rapid bone induction relative to induction of bone within a segmental defect.

The process of distraction osteogenesis begins with an initial latency period allowing a fibrous connection to form between the bone ends to be distracted. Following this latency period, the bone ends are slowly distracted at a controlled rate of up to 1 mm per day in human clinical cases. Once the regenerate forms and the bone ends are distracted to the appropriate length, a prolonged consolidation period is required to allow the regenerate to form bone. This prolonged consolidation period which can be on the order 4 to 6 months is associated with considerable morbidity. A frequent complication is the occurrence of pin track infections resulting from the extended length of time the external fixator used to generate the distraction must remain in place. In addition, there are considerable psychological effects and life style alterations associated with wearing the external fixator for prolonged periods of time. In addition to complications associated with the external fixator, there are a number of patients where the regenerate does not form properly and a delayed union or non-union occurs. Since the regenerate contains a responsive cell population and is already highly vascularized following the initial distraction phase, the use of bone morphogenetic proteins may rapidly accelerate the rate of bone formation during the normally prolonged consolidation phase of distraction osteogenesis. Acceleration of the distraction phase is limited by stretching of the soft tissues associated with bone. The cells created using distraction osteogenesis may also be harvested in order to provide a source of cells that are primed for osteogenesis. These cells can be cultured to prepare immortalized cell lines. If desired, these cells can also be immunotolerized using agents such as CTLA4 receptors [U.S. Pat. No. 5,434,131] or CTLA4 ligands or B7 monoclonal antibodies [WO 96/40915]. Methods and materials for such immunotolerization are disclosed in the above references, and include co-transfection or treatment with these factors. The disclosure of these references is hereby incorporated herein by reference.

In addition to treating osteoporosis and closed fractures, the rod-shaped compositions of the present invention may also find application to other bone sites such as bone cysts and defects. Injectable solid compositions may also be administered to non-bone sites, for example into tendons, damaged cartilage tissue, ligaments, and/or their attachment sites to bones.

Although the foregoing discussion relates to the administration of a single osteoinductive composition, the present invention expressly contemplates the co-administration of multiple active ingredients in separate formulations, for example the bisphosphonate compositions described above. Multiple active ingredients may be delivered concurrently or sequentially in separate delivery vehicles, and individually or in combination.

The dosage regimen will be determined by the clinical indication being addressed, as well as by various patient variables (e.g., weight, age, sex) and clinical presentation (e.g., extent of injury, site of injury, etc.).

The compositions of the subject invention allow therapeutically effective amounts of osteoinductive protein to be delivered to an injury site where cartilage and/or bone formation is desired. The formulations may be used as a substitute for autologous bone graft in fresh and non-union fractures, spinal fusions, and bone defect repair in the orthopaedic field; in cranio/maxillofacial reconstructions; in osteomyelitis for bone regeneration; and in the dental field for augmentation of the alveolar ridge and periodontal defects and tooth extraction sockets. When used to treat osteomyelitis or for bone repair with minimal infection, the osteogenic protein may be used in combination with antibiotics. The antibiotic is selected for its ability to decrease infection while having minimal adverse effects on bone formation. Preferred antibiotics for use in the compositions of the present invention include vancomycin and gentamycin. The antibiotic may be in any pharmaceutically acceptable form, such as vancomycin HCl or gentamycin sulfate. The antibiotic is preferably present in a concentration of from about 0.1 mg/mL to about 10.0 mg/mL. The traditional preparation of formulations in pharmaceutically acceptable form (i.e., pyrogen free, appropriate pH and isotonicity, sterility, etc.) is well within the skill in the art and is applicable to the formulations of the invention.

The solid rod-shaped compositions of the present invention may also be utilized in combination with other drugs, growth factors, peptides, proteins, cytokines, oligonucleotides, antisense oligonucleotides, DNA and polymers. These compounds may be added by mixing them with the hyaluronic acid carrier or by covalent attachment to the carriers. The hyaluronic acid compositions may also be used with DNA encoding for BMPs and cells transduced or transfected with genes encoding BMP proteins.

The following examples are illustrative of the present invention and are not limiting in any manner. Modifications, variations and minor enhancements are contemplated and are within the present invention.

Example 1

Formulation of HYAFF-11® Rods

Injectable 100% esterified HYAFF-11® rod-shaped compositions (1 mm in diameter) were prepared and evaluated for recombinant human bone morphogenetic protein-2 (rhBMP-2) retention and bone formation efficacy. The rod-shaped compositions comprised HYAFF-11® hyaluronan-based material as carrier, two doses (see Table 1) of rhBMP-2 as active ingredient, and varying amounts of excipients for modulation of release kinetics. Excipients used in this example consisted of dry powder forms of either glutamic acid or buffer salts. Buffer salts contained 0.5% sucrose, 2.5% glycine, 5 mM L-glutamic acid, 5 mM NaCl, and 0.01% polysorbate 80. The Hyaff-11® based compositions were formed into rod shapes using a phase inversion process. Briefly, rhBMP-2 and excipients (glutamate and buffer salts) were mixed into pre-solubilized HYAFF-11® particulates (10% w/v) in organic solvent N-methylpyrrolidone (NMP), extruded into excess ethanol (nonsolvent) using a syringe and a catheter (e.g., 16-gauge), phase inverted for 1 hour, rinsed, and dried. The drying step consisted of 24 hour air-drying followed by a 24 hour lyophilization step. Extrusion was performed using a metered syringe pump, preferably at 0.2 mL/min injection rate. The following HYAFF-11®-based compositions were prepared: HYAFF-11®, 20% (w/w) rhBMP-2, and 40% (w/w) glutamate (i.e., 40/40/20 (w/w) HYAFF-11®/glutamate/rhBMP-2); HYAFF-11®, 60% (w/w) rhBMP-2/buffer salts (i.e., 40/60 (w/w) HYAFF-11®/rhBMP-2); and HYAFF-11®, 20% (w/w) rhBMP-2, and 20% (w/w) buffer salts (i.e., 60/20/20 (w/w) HYAFF-11®/buffer salts/rhBMP-2). High rhBMP-2 doses were obtained by desalting the protein formulation prior to combination with the Hyaff-11. Dried rods were typically cut into 1 or 2 cm segments for further evaluation. The theoretical doses of the rods are listed in Table 1. The preferred mode of administration is a 16-gauge hypodermic needle equipped with an obdurator to inject the solid rods into the intraosseous site.

TABLE 1 rhBMP-2 Doses for Injectable HYAFF ® Rod Formulations

| Formulation | Theoretical Dose | |
|---|---|---|
| | (µg BMP-2/mg rod) | (mg BMP-2/cm rod) |
| 40/40/20 (w/w) HYAFF-11 ®/Glutamate/rhBMP-2 | 200 | 1.5 |
| 40/60 (w/w) HYAFF-11 ®/rhBMP-2 | 71 | 0.5 |
| 60/20/20 (w/w) HYAFF-11 ®/buffer salts/rhBMP-2 | 200 | 1.3 |
| 80/20 (w/w) HYAFF-11P65 ®/rhBMP-2 | 200 | 1.2 |
| 60/40 (w/w) HYAFF-11P65 ®/rhBMP-2 | 400 | 2.4 |

Example 2

Formulation of HYAFF-11P65® Rods

Injectable 65% esterified Hyaff-11p65 rod-shaped compositions (1 mm in diameter) were prepared and evaluated for rhBMP-2 retention and bone formation efficacy. The rod-shaped compositions comprised HYAFF-11P65® hyaluronan-based material as carrier and two doses (see Table 1) of rhBMP-2 as active ingredient. HYAFF-11P65®-based compositions comprising 20% (w/w) rhBMP-2 (i.e., 80/20 (w/w) HYAFF-11P65®/rhBMP-2) or 40% (w/w) rhBMP-2 (i.e., 60/40 (w/w) HYAFF-11P65®/rhBMP-2) were prepared by mixing desalted rhBMP-2 and HYAFF-11P65® non-woven pads in dry forms, followed by hydrating to 18.75% (w/v) of the weight of the non-woven pad, mixing to a white paste-like consistency, transferring to a syringe, extruding through a catheter (e.g., 16-gauge), and drying. A variation of this method consists of extruding the paste through a catheter to a rod form, freezing the rod (in −80° C. or liquid nitrogen), inserting into a slightly larger diameter tubing (e.g., 14-gauge catheter), and drying. The drying step consisted of 24 hour air-drying followed by a 24 hour lyophilization step. Alternative methods of rod preparation include molding the HYAFF-11P65® paste into a 1.5 mm inner-diameter silastic or TEFLON®/FEP tubing followed by drying. The preferred mode of administration is a 16-gauge hypodermic needle equipped with an obdurator to force the solid rods into the intraosseous site.

Example 3

In Vitro Characterization

All rod-shaped compositions were rigid, straight, handleable, and injectable through a 16-gauge needle. Scanning electron micrographs (SEM) of HYAFF-11® rod compositions were typically solid, dense, and smooth, while those of HYAFF-11P65® rod compositions were densely packed with short, fibrillar segments of the native non-woven fibers. Bioactivity of rhBMP-2 in the rod-shaped compositions was obtained after extracting rhBMP-2 from the compositions and testing its ability to induce alkaline phosphatase (a bone marker) expression in mouse W-20-17 stromal cells. The rhBMP-2 from HYAFF-11® and HYAFF-11P65® rod compositions were bioactive.

Example 4

In Vivo Local Biodistribution

Figure 1:
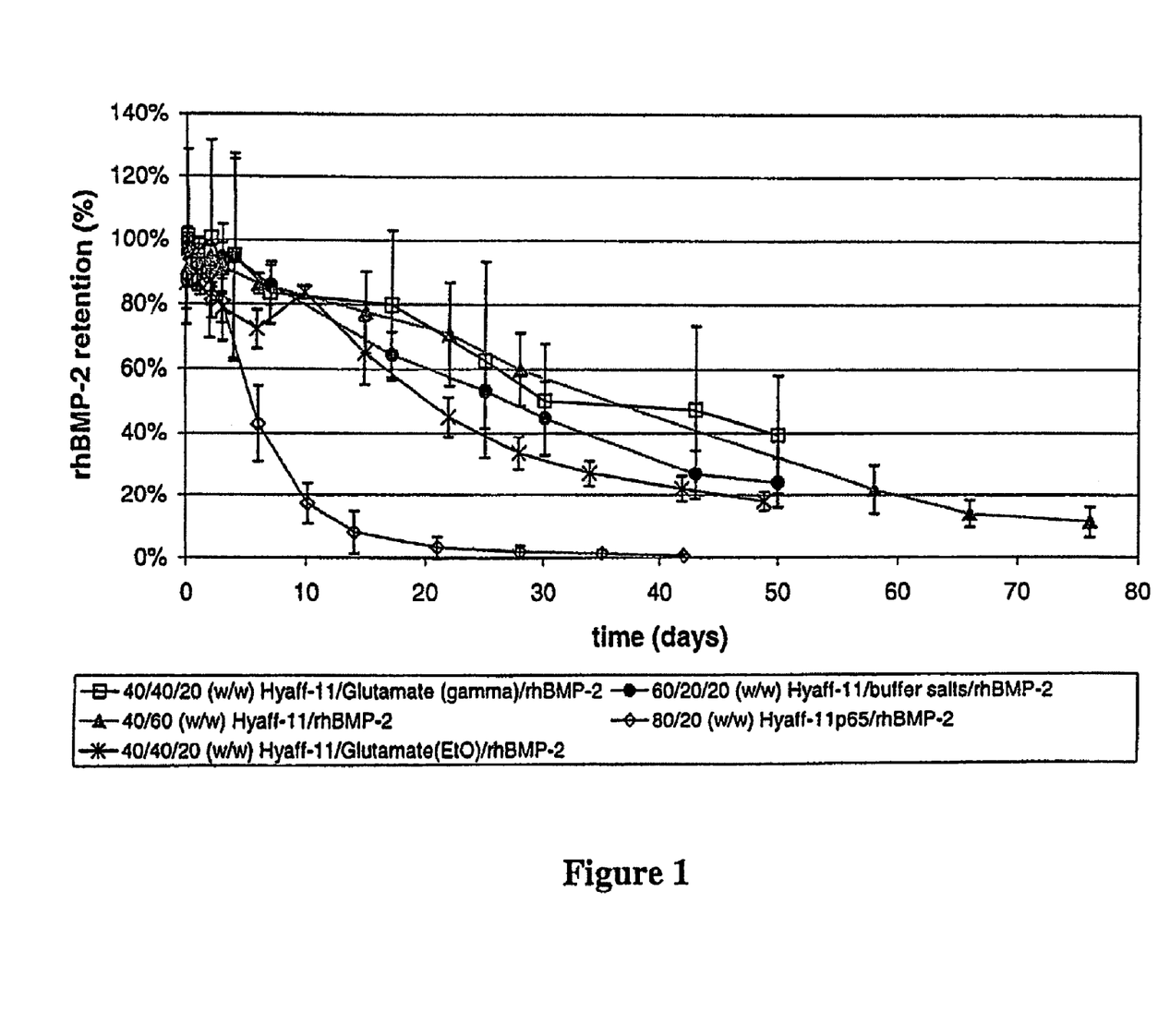
FIG. 1 is a graph showing the local retention times of BMP-2 for various hyaluronic acid/rhBMP-2 compositions in the rabbit distal femur (intraosseous) model.

A range of in vivo rhBMP-2 retention profiles were obtained using HYAFF-11® and HYAFF-11P65® rod compositions. Local retention times of rhBMP-2 in 1 cm rod-shaped compositions (prepared as described in Example 1 and 2) were evaluated in a rabbit distal femur intraosseous model using $^{125}$I-rhBMP-2 and gamma scintigraphy (FIG. 1). Formulations comprising HYAFF-11® (not HYAFF-11P65®) provided slow, sustained release of rhBMP-2, regardless of BMP-2 dose or excipients. Sterilization of the glutamate excipient by ethylene oxide provided a slightly more burst release during the initial 3-day period as compared to gamma-sterilized glutamate. The 80/20 (w/w) HYAFF-11P65®/rhBMP-2 composition provided the fastest release kinetics of rhBMP-2.

Example 5

Efficacy and Biocompatibility

The HYAFF-11®-based compositions (not HYAFF-11P65®), prepared as described above, were evaluated for biocompatibility and effect on bone formation two weeks following subcutaneous (ventral thorax) and intraosseous (distal femur) administration in rats. The rod-shaped compositions were 2 mm and 10 mm in length for intraosseous and subcutaneous administration, respectively. Radiographic and histologic analysis of subcutaneous sites of administration showed bone formation adjacent to the rod-shaped compositions containing rhBMP-2, suggesting that rhBMP-2/HYAFF-11® rods were osteoinductive (data not shown). Both subcutaneous and intraosseous sites of administration showed minimum inflammatory responses, suggesting good biocompatibility of the hyaluronic acid/BMP-2 compositions. The HYAFF-11® and HYAFF-11P65® rod compositions were additionally injected into rabbit distal femurs and after 7 weeks, considerable de novo bone formation in the intraosseous space was observed by histology (data not shown) and particularly in the 80/20 (w/w) HYAFF-11P65®/rhBMP-2 and 40/40/20 (w/w) HYAFF-11®/glutamate/rhBMP-2 formulations. Injection of 80/20 (w/w) HYAFF-11P65®/rhBMP-2 rod formulation into the distal radius of ovariectomized baboons resulted in a 30% relative increase in total bone volume compared to untreated controls histologically (data not shown).

We claim:

1. A method of treating a bone defect in a mammal comprising administering to the site of bone defect an effective amount of a composition in the form of a solid cylindrical rod suitable for intraosseous injection into a body, wherein said composition comprises an osteogenic protein and a hyaluronic acid ester.

2. The method of claim 1, wherein the osteogenic protein is selected from the group consisting of BMP-2, BMP-4, BMP-5, BMP-6, BMP-7, BMP-10, BMP-12, BMP-13, or MP52.

3. The method of claim 1, wherein the osteogenic protein is BMP-2.

4. The method of claim 1, wherein the osteogenic protein is BMP-6.

5. The method of claim 1, wherein the osteogenic protein is BMP-12.

6. The method of claim 1, wherein the osteogenic protein is BMP-13.

7. The method of claim 1, wherein the osteogenic protein is MP52.

8. The method of claim 1, further comprising a bone resorption inhibitor.

9. The method of claim 1, wherein the bone resorption inhibitor is a bisphosphonate.

10. The method of claim 1, wherein the bisphosphonate is selected from the group consisting of alendronate, cimadronate, clodronate, EB-1053, etidronates, ibandronate, neridronate, olpadronate, pamidronate, risedronate, tiludronate, YH 529, zolendronate, and pharmaceutically acceptable salts, esters, acids, and mixtures thereof.

11. The method of claim 1, wherein the hyaluronic acid ester comprises from about 50 percent to about 100 percent hyaluronic acid esterification.

12. The method of claim 1, wherein the hyaluronic acid is a 65% esterified hyaluronic acid.

13. The method of claim 1, wherein the hyaluronic acid ester is a cross-linked hyaluronic acid.

14. The method of claim 1, wherein the diameter of the cylindrical rod is between about 0.5 to 1.5 mm.

15. The method of claim 1, wherein the length of the cylindrical rod is between about 2 cm and about 5 cm.

16. The method of claim 1, wherein administration of the rod reduces the risk of embolism in comparison to administration of a liquid or paste.

17. A method of treating a bone defect in a mammal comprising administering to the site of bone defect an effective amount of a composition for treating osteoporotic bone prepared by a process comprising the steps of:
   (a) mixing an osteogenic protein and an hyaluronic acid ester to form an osteogenic mixture; and
   (b) forming and drying the osteogenic mixture into a cylindrical rod suitable for intraosseous injection in solid state into a body.

18. The method of claim 17, wherein the step of mixing further comprises mixing the osteogenic protein and hyaluronic acid ester with a bone resorption inhibitor.

19. The method of claim 18, wherein the bone resorption inhibitor is a bisphosphonate.

20. The method of claim 18, wherein the bisphosphonate is selected from the group consisting of alendronate, cimadronate, clodronate, EB-1053, etidronate, ibandronate, neridronate, olpadronate, pamidronate, risedronate, tiludronate, YH 529, zolendronate, and pharmaceutically acceptable salts, esters, acids, and mixtures thereof.

21. The method of claim 17, wherein the hyaluronic acid ester is prepared by hydration or solubilization of insoluble or partially soluble particles, films, fibers, non-woven pads, or sponges of hyaluronic acid benzyl esters in water, an organic solvent, or an aqueous buffer.

22. The method of claim 17, wherein the osteogenic protein is selected from the group consisting of BMP-2, BMP-4, BMP-5, BMP-6, BMP-7, BMP-10, BMP-12, BMP-13, and MP52.

23. The method of claim 17, wherein the step of mixing comprises mixing the osteogenic protein and hyaluronic acid ester with a solvent; and wherein the step of forming and drying the osteogenic mixture into a cylindrical rod comprises extruding the osteogenic mixture in a nonsolvent.

24. The method of claim 17, where in the step of forming and drying the osteogenic mixture comprises extruding the osteogenic mixture in a nonsolvent.

25. The method of claim 24, wherein the hyaluronic acid ester is water insoluble and the nonsolvent is ethanol or water.

26. The method of claim 17, where in the step of forming and drying the osteogenic mixture comprises extruding the osteogenic mixture into air and drying.

27. The method of claim 17, wherein an embolism is less likely than if the composition were in a liquid or gel state.

* * * * *

UNITED STATES PATENT AND TRADEMARK OFFICE
CERTIFICATE OF CORRECTION

| | | |
|---|---|---|
| PATENT NO. | : 7,875,590 B2 | Page 1 of 1 |
| APPLICATION NO. | : 12/414715 | |
| DATED | : January 25, 2011 | |
| INVENTOR(S) | : Rebecca H. Li et al. | |

It is certified that error appears in the above-identified patent and that said Letters Patent is hereby corrected as shown below:

On the Title Page, Item (62), in the "Related U.S. Application Data",
line 1, after "No. 10/525,441," and before "filed as", insert
--which entered the national stage on Feb. 22, 2005,--.

In claim 17, column 17, line 12, "an hyaluronic" should read --a hyaluronic--.

In claim 26, column 18, line 20, "where in" should read --wherein--.

Signed and Sealed this
Third Day of May, 2011

David J. Kappos
*Director of the United States Patent and Trademark Office*